United States Patent
Anderson et al.

(10) Patent No.: US 8,521,293 B2
(45) Date of Patent: *Aug. 27, 2013

(54) MEASUREMENT OF PATIENT PHYSIOLOGICAL PARAMETERS

(75) Inventors: Russell Eugene Anderson, Hopkins, MN (US); Nadim Yared, Medina, MN (US); John Charles Stroebel, Blaine, MN (US); Robert S Kieval, Medina, MN (US); Steve Check, Eden Prairie, MN (US); Eric Lovett, Mendota Heights, MN (US)

(73) Assignee: CVRx, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,412

(22) Filed: Feb. 13, 2012

(65) Prior Publication Data

US 2012/0149998 A1  Jun. 14, 2012

Related U.S. Application Data

(63) Continuation of application No. 12/345,558, filed on Dec. 29, 2008, now Pat. No. 8,116,873.

(60) Provisional application No. 61/017,496, filed on Dec. 28, 2007, provisional application No. 61/018,188, filed on Dec. 31, 2007.

(51) Int. Cl.
*A61N 1/36* (2006.01)
*A61N 1/365* (2006.01)

(52) U.S. Cl.
USPC ............ 607/44; 607/17; 600/547; 600/301

(58) Field of Classification Search
USPC ............ 600/436, 345, 547; 607/44, 62
See application file for complete search history.

(56) References Cited

U.S. PATENT DOCUMENTS

| 5,707,400 | A | 1/1998 | Terry, Jr. et al. |
| 5,800,468 | A | 9/1998 | Holmstrom |
| 6,115,633 | A * | 9/2000 | Lang et al. ............. 607/17 |
| 6,522,926 | B1 | 2/2003 | Kieval et al. |

(Continued)

FOREIGN PATENT DOCUMENTS

| WO | WO 2004/075928 A2 | 9/2004 |
| WO | WO 2006/031902 A2 | 3/2006 |
| WO | WO 2007/136851 A2 | 11/2007 |

OTHER PUBLICATIONS

U.S. Appl. No. 12/345,558, filed Dec. 29, 2008; Robert S. Kieval.

(Continued)

*Primary Examiner* — Carl H Layno
*Assistant Examiner* — Jon Eric C Morales
(74) *Attorney, Agent, or Firm* — Patterson Thuente Pedersen, P.A.

(57) ABSTRACT

A method of determining one or more physiological parameter of a patient by providing a plurality of implantable electrodes proximate a blood vessel of the patient, applying a measurement signal through the plurality of electrodes, the measurement signal having a known parameter, obtaining a resultant signal through the plurality of electrodes, the resultant signal having a resultant parameter, calculating vascular impedance based on the measurement signal and the resultant signal, and calculating a physiological parameter based on the vascular impedance. In some embodiments, the physiological parameter is utilized to modify a therapy signal controlling therapy delivered to the patient.

21 Claims, 12 Drawing Sheets

(56) References Cited

U.S. PATENT DOCUMENTS

| | | |
|---|---|---|
| 6,985,774 B2 | 1/2006 | Kieval et al. |
| 7,580,746 B2 | 8/2009 | Gilkerson et al. |
| 7,643,875 B2 | 1/2010 | Heil, Jr. |
| 7,647,114 B2 | 1/2010 | Libbus |
| 7,873,413 B2 | 1/2011 | McCabe et al. |
| 8,116,873 B2 | 2/2012 | Anderson et al. |
| 8,321,024 B2 | 11/2012 | Georgakopoulos et al. |
| 8,326,430 B2 | 12/2012 | Gerogakopoulos et al. |
| 2002/0058877 A1 | 5/2002 | Baumann et al. |
| 2002/0151816 A1 | 10/2002 | Rich et al. |
| 2003/0149450 A1 | 8/2003 | Mayberg |
| 2004/0102712 A1 | 5/2004 | Belaleazar et al. |
| 2004/0176672 A1 | 9/2004 | Silver et al. |
| 2004/0220632 A1 | 11/2004 | Burnes |
| 2005/0143779 A1 | 6/2005 | Libbus |
| 2005/0154418 A1 | 7/2005 | Kieval et al. |
| 2005/0251033 A1 | 11/2005 | Scarantino et al. |
| 2005/0251212 A1 | 11/2005 | Kieval et al. |
| 2006/0004417 A1 | 1/2006 | Rossing et al. |
| 2006/0047218 A1 | 3/2006 | Bloom et al. |
| 2006/0074453 A1 | 4/2006 | Kieval et al. |
| 2006/0089678 A1 | 4/2006 | Shalev |
| 2006/0094967 A1 | 5/2006 | Bennett et al. |
| 2006/0282145 A1 | 12/2006 | Caparso et al. |
| 2006/0293712 A1 * | 12/2006 | Kieval et al. ............... 607/2 |
| 2007/0021792 A1 | 1/2007 | Kieval et al. |
| 2007/0156061 A1 | 7/2007 | Hess |
| 2009/0036777 A1 | 2/2009 | Zhang et al. |
| 2009/0132002 A1 | 5/2009 | Kieval |
| 2009/0143837 A1 | 6/2009 | Rossing et al. |
| 2009/0198302 A1 | 8/2009 | Anderson et al. |
| 2010/0004714 A1 | 1/2010 | Georgakopoulos et al. |
| 2012/0095523 A1 | 4/2012 | Yared |
| 2012/0123506 A1 | 5/2012 | Georgakopoulos et al. |
| 2013/0030309 A1 | 1/2013 | Yared et al. |

OTHER PUBLICATIONS

International Preliminary Report on Patentability of PCT/US/2008/088488; 8 pages; Jul. 8, 2010.

Application and File history for U.S. Appl. No. 13/682,317, filed Nov. 20, 2012. Inventors: Anderson et al.

Extended European Search Report, EP Application No. 08868910.4, Dec. 20, 2012, 9 pages.

* cited by examiner

MEASUREMENT OF PATIENT PHYSIOLOGICAL PARAMETERS

RELATED APPLICATIONS

The present application is a continuation of U.S. application Ser. No. 12/345,558, entitled "Measurement Of Patient Physiological Parameters," filed Dec. 28, 2008, now U.S. Pat. No. 8,116,873, which claims the benefit of U.S. Provisional Patent Application Nos. 61/017,496, entitled "Measurement of Patient Physiological Parameters," filed Dec. 28, 2007, and 61/018,188, entitled "Real Time Feedback for Baroreflex Therapy," filed Dec. 31, 2007, the disclosures of which are hereby incorporated by reference in their entireties.

FIELD OF THE INVENTION

The present invention relates generally to monitoring physiologic parameters of a patient. More specifically, the present invention relates to devices and methods for determining physiological parameters of a patient from the impedance measurement of a blood vessel.

BACKGROUND OF THE INVENTION

Cardiovascular diseases and disorders are a major contributor to patient illness and mortality. They are also a primary driver of health care expenditure, costing billions of dollars each year in the United States. Common cardiovascular diseases and disorders include hypertension, ischemic heart disease, heart failure, and others. Hypertension, or high blood pressure, is a major cardiovascular disorder that is estimated to affect 65 million people in the United States alone. Of those with hypertension, it is reported that fewer than 30% have their blood pressure under control. Hypertension is a leading cause of heart failure and stroke. It is the primary cause of death for tens of thousands of patients per year and is listed as a primary or contributing cause of death for hundreds of thousands of patients per year in the U.S. Accordingly, hypertension is a serious health problem demanding significant research and development for the treatment thereof.

Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. Heart failure is characterized by an inability of the heart to pump enough blood to meet the body's needs and results in fatigue, reduced exercise capacity and poor survival. Heart failure results in the activation of a number of body systems to compensate for the heart's inability to pump sufficient blood. Many of these responses are mediated by an increase in the level of activation of the sympathetic nervous system, as well as by activation of multiple other neurohormonal responses.

Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

A number of drug treatments have been proposed for the management of hypertension, heart failure and other cardiovascular disorders. These include vasodilators to reduce the blood pressure and ease the workload of the heart, diuretics to reduce fluid overload, inhibitors and blocking agents of the body's neurohormonal responses, and other medicaments.

Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month. Cardiac resynchronization therapy (CRT) may be used to improve the coordination of the heart's contractions. Other surgical procedures are available as well.

It is known that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through activation of the sympathetic nervous system. Electrical stimulation of the carotid sinus nerve (baropacing) has previously been proposed to reduce blood pressure and the workload of the heart in the treatment of high blood pressure and angina. For example, U.S. Pat. No. 6,073,048 to Kieval et al. discloses a baroreflex modulation system and method for stimulating the baroreflex arc based on various cardiovascular and pulmonary parameters. Implantable devices for treating high blood pressure or hypertension by stimulating various nerves and tissue in the body are known and described, for example, in U.S. Pat. No. 3,650,277 (stimulation of carotid sinus nerve), U.S. Pat. No. 5,707,400 (stimulation of vagal nerve), and U.S. Pat. No. 6,522,926 (stimulation of baroreceptors).

Regardless of the treatment given to a patient, it is often desirable to monitor various physiological parameters of the patient, especially in conjunction with a delivered therapy. With implantable devices, physiological measurement and diagnostic data gathering may be done independently of therapy stimulation. For example, in a cardiac rhythm management device a dedicated sense amplifier channel is often implemented separately from the stimulation output channel, so that physiological measurements of heart rate, P-wave amplitude, R-wave amplitude, and QRS interval are done independently of device stimulation. The stimulation output is also independent of the monitoring of physiologic parameters such as minute ventilation, for which impedance measurements are taken across a pair of electrodes typically positioned at a distance suitable for a transthoracic measurement and not directly used for stimulation. The dedicated sense electrodes are excited with a signal source not used in the actual therapy. The signal sources for this kind of sensing are typically very low in amplitude and can cover a large stimulation vector.

Other current methods of measuring patient physiologic parameters such as blood pressure include direct intravascular or external blood pressure cuff determinations. Direct intravascular measurement is accomplished using complicated, discrete sensors separately located within the body, which require additional circuitry to be implanted into the body and may create difficulties for measuring the parameters in real time. Blood pressure measurement by an external cuff such as a sphygmomanometer allows for only sporadic monitoring.

The above methods each have their own disadvantages. Accordingly, it would be desirable for improved devices and methods to monitor patient physiologic parameters, either as a stand-alone device or combined with a delivered therapy.

SUMMARY OF THE INVENTION

In one embodiment, the present invention comprises a method of determining a physiological parameter of a patient, comprising providing a plurality of implantable electrodes proximate a blood vessel of the patient, applying a measurement signal through the plurality of electrodes, the measurement signal having a known parameter, obtaining a resultant signal through the plurality of electrodes, the resultant signal having a resultant parameter, calculating vascular impedance based on the measurement signal and the resultant signal, and calculating a physiological parameter based on the vascular impedance.

In another embodiment, the present invention comprises a method of measuring blood pressure, comprising providing a plurality of implantable electrodes proximate a blood vessel of a patient, determining the impedance of the blood vessel, and calculating blood pressure based on the determined blood vessel impedance.

In a further embodiment, the present invention comprises a system, comprising a therapy device, at least one pair of implantable electrodes proximate a blood vessel of a patient, and a controller communicably coupled to the therapy device and the electrodes, the controller configured to calculate the impedance of the blood vessel and determine a physiological parameter of the patient based on the impedance.

In one embodiment, the present invention comprises a method for providing therapy having real-time feedback, comprising transmitting a therapy signal to a therapy device having one or more electrodes on or about a blood vessel, the therapy signal having at least one known parameter, monitoring a resultant signal with the therapy device, the resultant signal having a resultant parameter, calculating the impedance of the blood vessel based on the known parameter and the resultant parameter, determining one or more physiological parameters based on the impedance of the blood vessel, and adjusting the therapy based on the one or more physiological parameters.

BRIEF DESCRIPTION OF THE DRAWINGS

The invention may be more completely understood in consideration of the following detailed description of various embodiments of the invention in connection with the accompanying drawings, in which.

Figure 1:
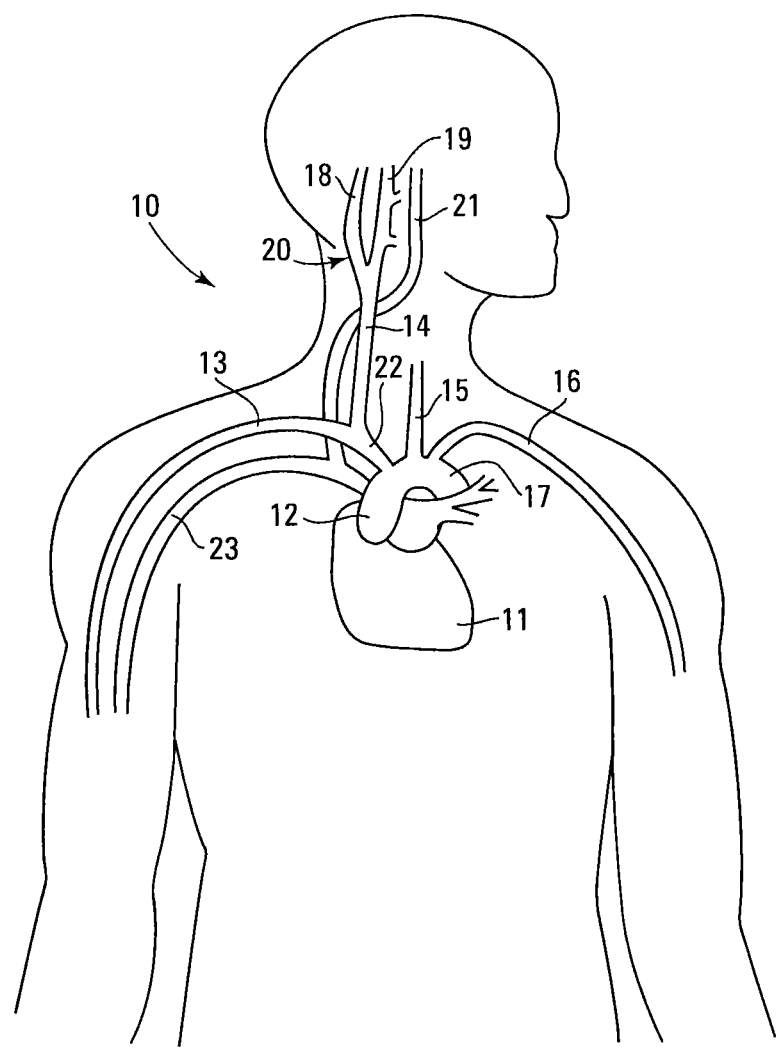
FIG. 1 is a schematic illustration of the upper torso of a human body showing the major arteries and veins and associated anatomy.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 15, 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. The heart 11 pumps the oxygen depleted blood through the pulmonary system where it is re-oxygenated. The re-oxygenated blood returns to the heart 11 which pumps the re-oxygenated blood into the aortic arch as described above, and the cycle repeats.

Figures 2A, 2B:
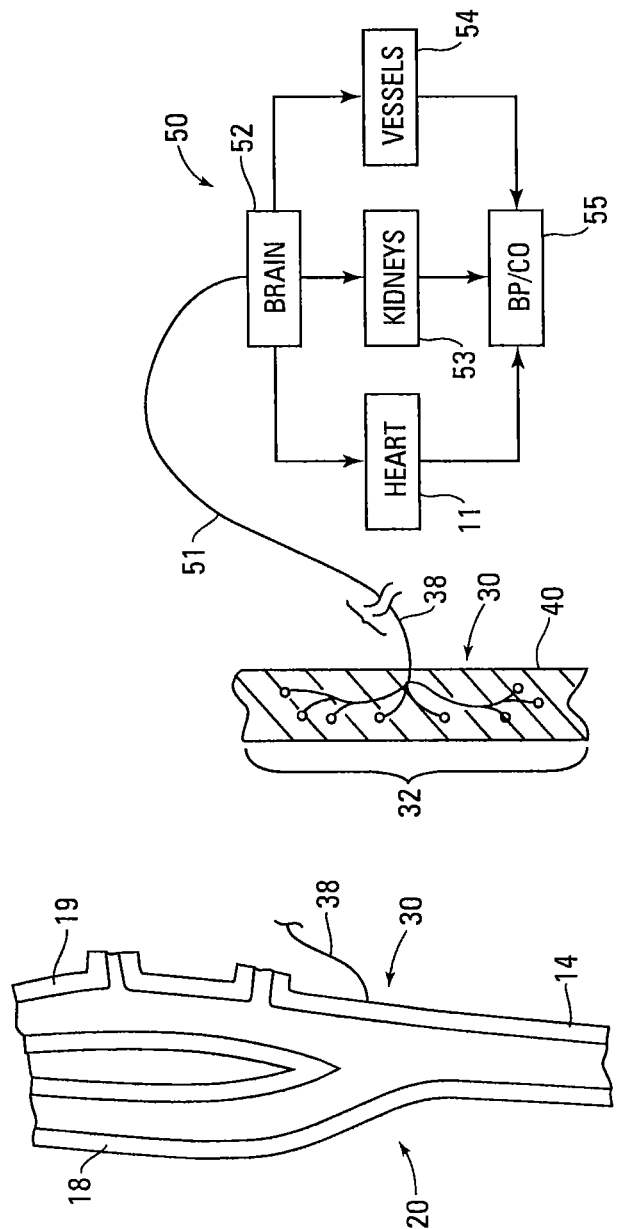
FIG. 2A is a cross-sectional schematic illustration of the carotid sinus and baroreceptors within the vascular wall.
FIG. 2B is a schematic illustration of baroreceptors within the vascular wall and the baroreflex system.

Within the arterial walls of the aortic arch 12, common carotid arteries 14/15 (near the right carotid sinus 20 and left carotid sinus), subclavian arteries 13/16, brachiocephalic artery 22, and other arteries, veins and cardiac structures, there are baroreceptors 30. For example, as best seen in FIG. 2A, within the walls of many veins, the pulmonary vasculature and the chambers of the heart, as in the walls of the carotid sinus, aorta and other arterial structures, there are baroreceptors 30. Baroreceptors 30 are a type of stretch receptor used by the body to sense blood pressure and blood volume. An increase in blood pressure or volume causes the vascular wall to stretch, and a decrease in blood pressure or volume causes the vascular wall to return to its original size. In many vessels, such a cycle is repeated with each beat of the heart. In others, in particular some of the body's veins, the pressure and volume change more slowly. Because baroreceptors 30 are located within the vascular wall, they are able to sense deformation of the adjacent tissue, which is indicative of a change in blood pressure or volume.

Refer now to FIG. 2B, which shows a schematic illustration of baroreceptors 30 disposed in a generic vascular wall 40 and a schematic flow chart of the baroreflex system 50. Baroreceptors 30 are profusely distributed within the vascular walls discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, those skilled in the art will appreciate that the baroreceptors 30 shown in FIG. 2B are primarily schematic for purposes of illustration and discussion.

Baroreflex modulation therapy is known to affect the body's autonomic nervous system, which in turn regulates the blood pressure, heart rate, respiration, and other systems. BAT may be used to activate baroreceptors to provide the brain with signals indicating an increase in blood pressure. These signals cause the brain to reduce the body's blood pressure and level of sympathetic nervous system and neurohormonal activation, and increase parasympathetic nervous system activation. The efficiency or effectiveness of baroreflex modulation therapy may be influenced by when it is delivered relative to the cardiac, respiratory and other respiratory cycles. For example, baroreflex modulation therapy may be more or less effective when delivered during the contraction vs. relaxation phase of the heart or during the expiratory vs. inspiratory phase of respiration. Accordingly, absolute measurements of arterial pressure or heart rate do not entirely reflect the full effects of baroreceptor stimulation.

The parasympathetic nervous system has a complementary relationship with the sympathetic nervous system. The body uses these two systems to regulate blood pressure. Stimulation or enhancement of the parasympathetic nervous system generally causes a decrease in blood pressure. Stimulating or enhancing the sympathetic nervous system, on the other hand, generally causes blood pressure to increase. If cardiac output is insufficient to meet demand (i.e., the heart is unable to pump sufficient blood), the brain activates a number of body systems, including the heart, kidneys, blood vessels, and other organs/tissues to correct this.

Baroreceptor signals in the arterial vasculature are used to activate a number of body systems which collectively may be referred to as the baroreflex system. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

While there may be small structural or anatomical differences among various receptors in the vasculature, for the purposes of some embodiments of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. Stimulation of the baroreflex system may be accomplished by stimulating such receptors, nerves, nerve fibers, or nerve endings, or any combination thereof.

Figure 3:
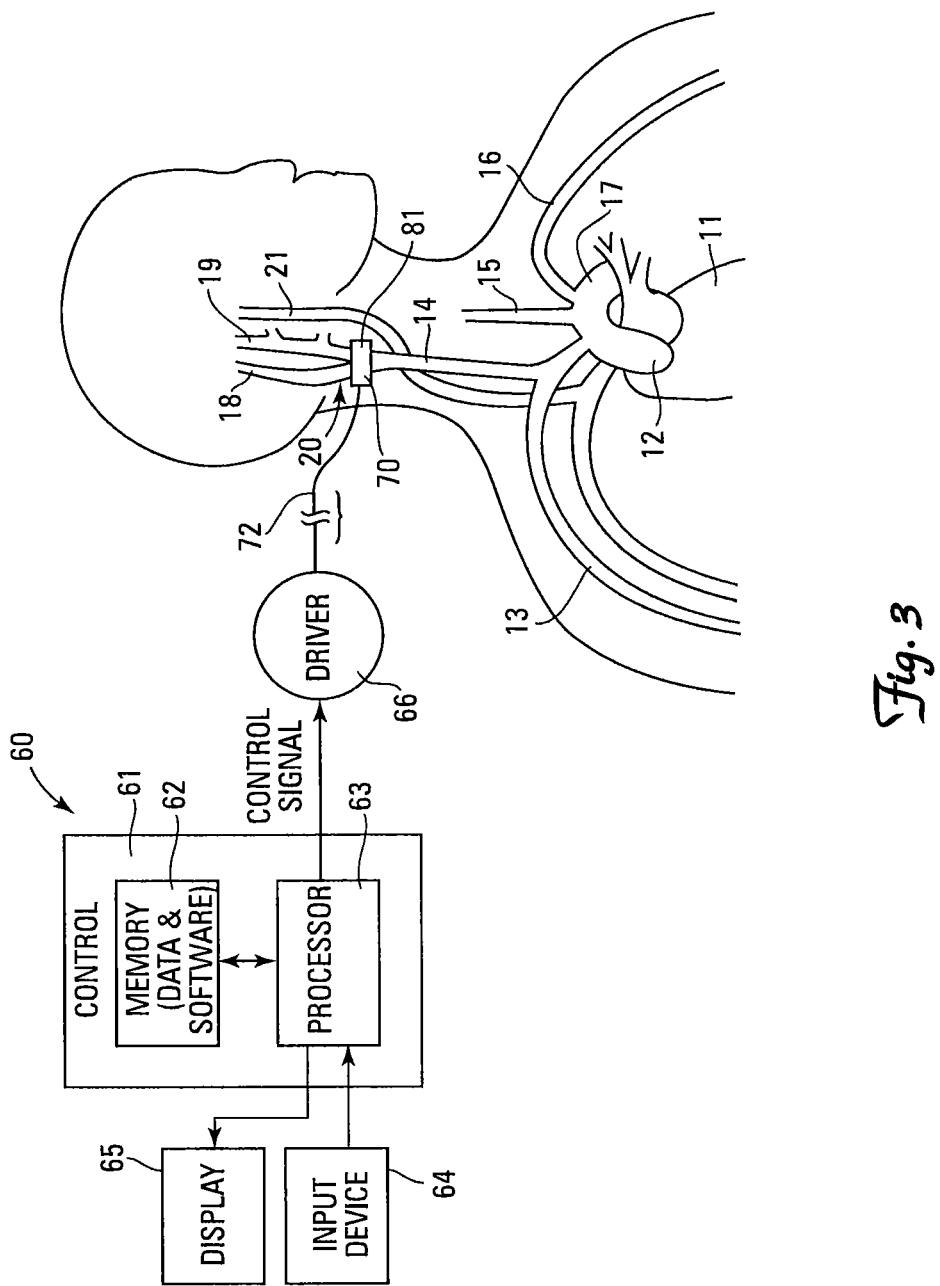
FIG. 3 is a schematic illustration of a baroreflex modulation system in accordance with the present invention.

Referring now to FIG. 3, an embodiment of a system for baroreflex therapy is depicted, including a control system 60, a baroreflex modulation device 70, and one or more sensor(s) 81. The control system 60 may include a therapy block 61 comprising a processor 63 and a memory 62. Control system 60 is communicably coupled to baroreflex modulation device 70 such as by way of electric control cable 72, or by wireless means such as RF. The sensor 81 may be combined and/or integrated with baroreflex modulation device 70, or sensor 81 may be separate from baroreflex modulation device 70 and communicably coupled to control system 60.

The control system memory 62 may contain data related to the sensor signal, the therapy signal, and/or values and commands provided by the input device 64. The memory 62 may also include software containing one or more algorithms defining one or more functions or relationships between the therapy signal and the sensor signal. The algorithm may dictate activation or deactivation therapy signals depending on the sensor signal or a mathematical derivative thereof. The algorithm may dictate an activation or deactivation therapy signal when the sensor signal falls below a lower predetermined threshold value, rises above an upper predetermined threshold value or when the sensor signal indicates a specific physiologic event. The memory 62 may also include software containing one or more algorithms for determining patient physiological parameters based on a measured parameter.

In one embodiment, the sensor(s) 81 senses and/or monitors a parameter, and generates a signal indicative of the parameter. The parameter may be related to cardiovascular function, and/or indicative of a need to modify the baroreflex system, and/or a physical parameter such as vascular impedance. The control system 60 receives the sensor signal from sensor 81 and transmits the therapy signal to the baroreflex modulation device 70 by way of control cable 72.

The control system 60 generates a control signal (also referred to as a therapy signal), which activates, deactivates or otherwise modulates or controls the baroreflex modulation device 70. In one embodiment, the therapy signal is in the range of about 1 to 10 volts, at a rate between 5 Hz and 200 Hz. Typically, activation of the device 70 results in activation of the baroreceptors 30. Alternatively, deactivation, modulation or other adjustments of the baroreflex modulation device 70 may cause or modify activation of the baroreceptors 30. The baroreflex modulation device 70 may include a wide variety of devices which utilize electrical means, such as electrodes, to activate baroreceptors 30.

The control system 60 may operate as a closed loop utilizing feedback from sensor 81, and/or optionally from other sensors, such as heart rate sensors, which may be incorporated. Control system 60 may also operate as an open loop utilizing reprogramming commands received by input device 64. The closed loop operation of the control system 60 preferably utilizes some feedback from the sensor(s), but may also operate in an open loop mode without feedback. In a closed loop embodiment, control system 60 generates a control signal as a function of the signal received from sensor 81 or other sensor. Thus, in one embodiment when sensor 81 detects a parameter indicative of the need to modify the baroreflex system activity (e.g., excessive blood pressure), the control system 60 generates a therapy signal to modulate (e.g., activate) the baroreflex modulation device 70 thereby inducing a baroreceptor 30 signal that is perceived by the brain 52 to be apparent excessive blood pressure. When the sensor 81 detects a parameter indicative of normal body function (e.g., normal blood pressure), the control system 60 generates a therapy signal to modulate (e.g., deactivate) the baroreflex modulation device 70.

Programming commands received by the input device 64 may directly influence the therapy signal, the output activation parameters, or may alter the software and related algorithms contained in memory 62. The treating physician and/or patient may provide commands to input device 64. In one embodiment, a display 65 may be used to view the sensor signal, therapy signal and/or the software/data contained in memory 62. Control system 60 may be implanted in whole or in part.

Baroreflex modulation device 70 is suitable for implantation, such as with a minimally invasive percutaneous translumenal approach and/or a minimally invasive surgical approach, depending on whether the device 70 is disposed intravascularly, extravascularly, transvascularly, within the vascular wall 40, or about the vascular sheath surrounding both the artery and vein. The baroreflex modulation device 70 may be positioned anywhere baroreceptors 30 affecting the baroreflex system 50 are numerous, such as in the heart 11, in the aortic arch 12, in the common carotid arteries 18/19 near the carotid sinus 20, in the subclavian arteries 13/16, brachiocephalic artery 22, or in the pulmonary artery, veins, or in or around the heart. The baroreflex modulation device 70 may be implanted such that the device 70 is positioned immediately adjacent the baroreceptors 30. In one embodiment, the baroreflex modulation device 70 is implanted near the right carotid sinus 20 and/or the left carotid sinus (near the bifurcation of the common carotid artery) and/or the aortic arch 12, where baroreceptors 30 have a significant impact on the baroreflex system 50. For purposes of illustration only, the present invention is described with reference to baroreflex modulation device 70 positioned near the carotid sinus 20.

Figure 13:
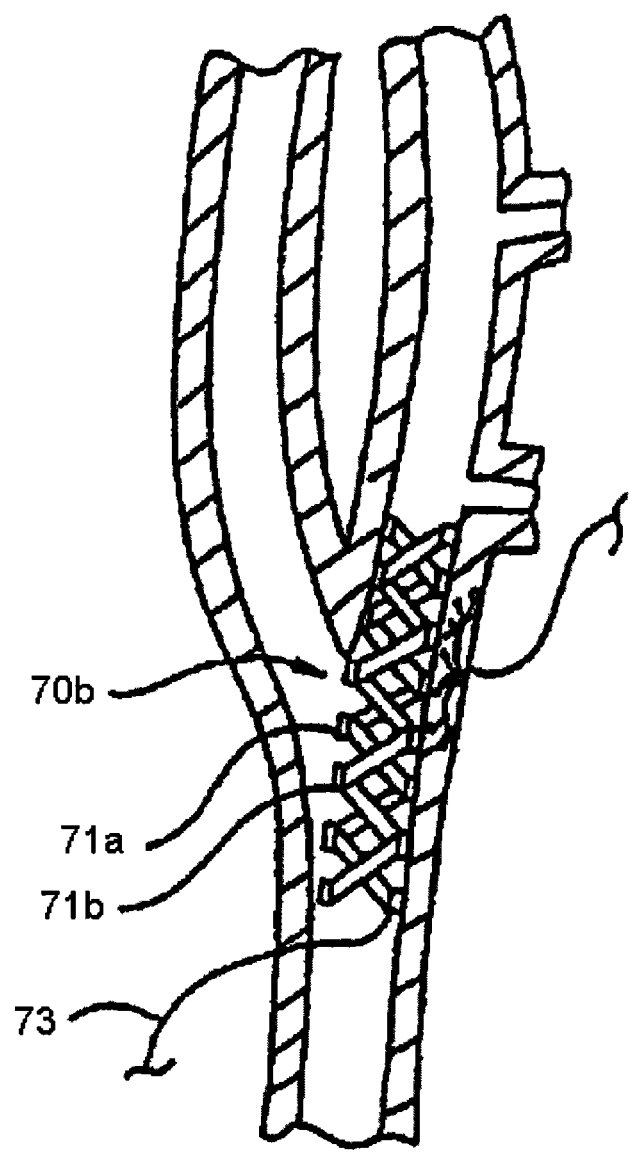
FIG. 13 is a schematic illustration of a baroreceptor activation device in the form of an internal bipolar conductive structure.

In one embodiment, baroreflex modulation device 70 is configured as an extravascular device. However, baroreflex modulation device 70 may also be configured or adapted to be utilized in intravascular and transvascular applications, and even about the vascular sheath surrounding both the artery and vein. An intravascular baroreflex modulation device 70 may comprise a stent-like structure, having a plurality of electrodes 71a, 71b disposed thereon. FIG. 13. depicts a baroreceptor activation device 70a in the form of an intravascular electrically conductive structure or electrode 70b. Electrode structure 70b includes two or more individual electrically conductive members 71a/71b which are electrically isolated at their respective cross-over points utilizing insulative materials. Each of the members 71a/71b is connected to a separate conductor contained within the electrical lead 73. Alternatively, a multipolar arrangement may be used wherein three or more electrically conductive members are included in the structure 70b. For example, a tripolar arrangement may be provided by one electrically conductive member having a polarity disposed between two electrically conductive members having the opposite polarity. A transvascular baroreflex modulation device 70 may be disposed substantially within a vein, such as the jugular vein, with one or more electrical leads passing from the vein to an adjacent artery, such as the carotid sinus, or simply transmitting energy across the venous wall to the adjacent arterial wall. The one or more leads may protrude into the wall of the adjacent artery, or may remain on the exterior of the artery. Baroreflex modulation device 70 may also be configured for placement around all or a portion of a vascular sheath structure surrounding at least one vein and one artery as well as associated nerve structures. In such an embodiment, the baroreflex modulation device may take any of the configurations described for the extravascular embodiments, but with a corresponding diameter to match the diameter of the sheath.

In addition to determining patient physiological parameters from sensor 81, a number of patient physiologic parameters may be determined by measuring the electrical impedance of a blood vessel with the use of electrodes spaced along and/or across the wall of the blood vessel. The electrical impedance of the vessel can be determined by applying a measurement signal having a known, constant parameter and monitoring a resultant signal having a resultant parameter. The measurement signal may comprise an alternating current (AC) signal, or a direct current (DC) signal, such as a biphasic pulsed DC signal. In one embodiment, the known parameter of the measurement signal comprises a constant voltage, while the resultant parameter of the resultant signal comprises electric current. In another embodiment, the known parameter of the measurement signal comprises a constant current, while the resultant parameter comprises voltage.

Figure 4:
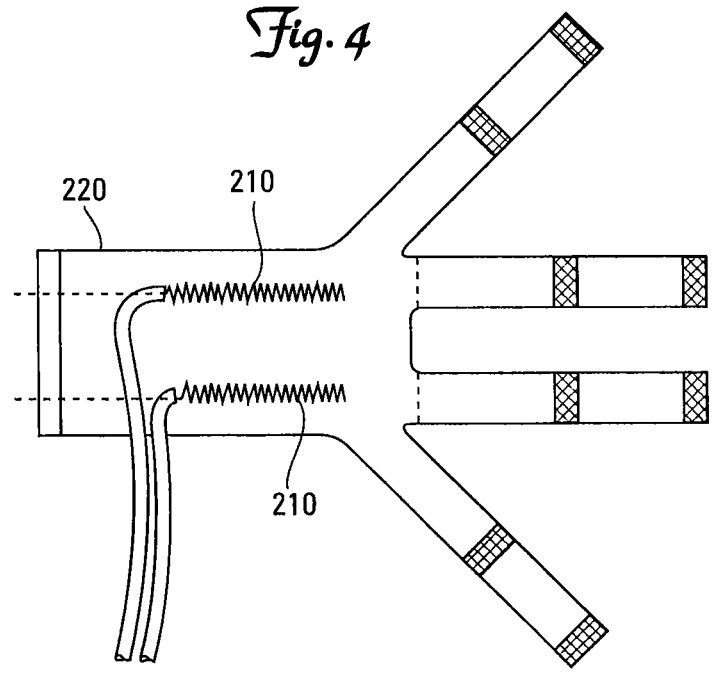
FIG. 4 is an embodiment of an extravascular measurement device according to one embodiment of the present invention.
Figure 5:
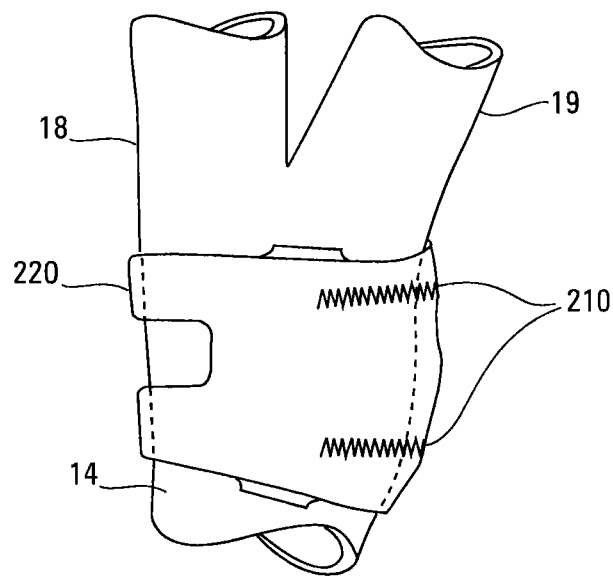
FIG. 5 is an embodiment of an extravascular measurement device implanted on a carotid artery according to one embodiment of the present invention.

The measurement signal can be transmitted through, and the monitored signal measured with, one or more implantable electrodes. The electrodes may be of the annular type, or unipolar point-type, or multi-polar, or other suitable type. In one embodiment depicted in FIG. 4, two diagnostic electrodes 210 are provided on extravascular wrap 220, which is configured to wrap around at least a portion of a blood vessel. Referring to FIG. 5, extravascular wrap 220 is implanted on common carotid artery 14, proximate the carotid sinus, such that electrodes 210 are longitudinally spaced from one other along the length of the blood vessel. In this embodiment, impedance is measured pervascularly, that is, along a length of a portion of the blood vessel. In an alternate embodiment not shown, electrodes 210 are spaced circumferentially around the vessel in the same plane. In an example of such an embodiment, the electrodes may be directly opposing one another such that the electrodes are spaced 180 degrees apart around the circumference of the vessel. The impedance is then measured transvascularly, that is, across at least part of the interior of the vessel. In a further embodiment, electrodes 210 may be spaced apart longitudinally as well as circumferentially on the blood vessel. In another embodiment, two or more measurement electrodes 210 are provided on or with an intravascular stent. Electrodes may be directly coupled to the intravascular stent, in which case the stent must be non-conductive, or measurement electrodes may be provided as part of an electrically insulative sleeve or wrap used in conjunction with the intravascular stent.

Although one suitable location for obtaining the impedance measurement is on the carotid artery near the carotid sinus, other suitable locations may include the femoral veins and arteries, the pulmonary artery, and the vasculature generally located within the torso. Other arteries and veins may also provide suitable locations for obtaining an impedance measurement.

In one embodiment, a single pair of electrodes is used to transmit the measurement signal, as well as pick up the resultant signal. In another embodiment, the electrode arrangement comprises a four-point kelvin arrangement, wherein a measurement signal is sent through a first pair of electrodes on the blood vessel, and the resultant signal is picked up by a second pair of electrodes.

The measurement signal may be continuous, periodic, episodic, random or a combination thereof. Continuous signals can include a constant pulse, a constant train of pulses, a triggered pulse and a triggered train of pulses. The measurement signal may also comprise a monophasic, biphasic, multiphasic, or alternating current waveform. The monitored resultant signal can be amplified, filtered, and decoded, then digitally processed to obtain one or more measured values. In one embodiment, transvascular impedance is determined from the voltage and current values using Ohm's Law, which states that voltage is proportional to electric current multiplied by impedance. The impedance then correlates to the volume of the blood vessel. A blood vessel section being monitored has a length L, between electrodes, and a cross sectional-area A. The volume of the vessel is equal to its length L, multiplied by its cross-sectional area A. However, the cross-sectional area of a blood vessel is difficult to accurately measure. The relationship $R=p*(L/A)$ can be used to calculate the area, where R is the impedance and p is the blood resistivity (a known constant). This allows the vessel portion volume to be calculated as $p*(L^2/R)$. The blood pressure can then be obtained, as it is proportional to the volume of the blood vessel section.

A number of experiments have been conducted to confirm the correlation between vascular impedance and patient physiological parameters such as blood pressure, heart rate, and respiration.

Figure 6:
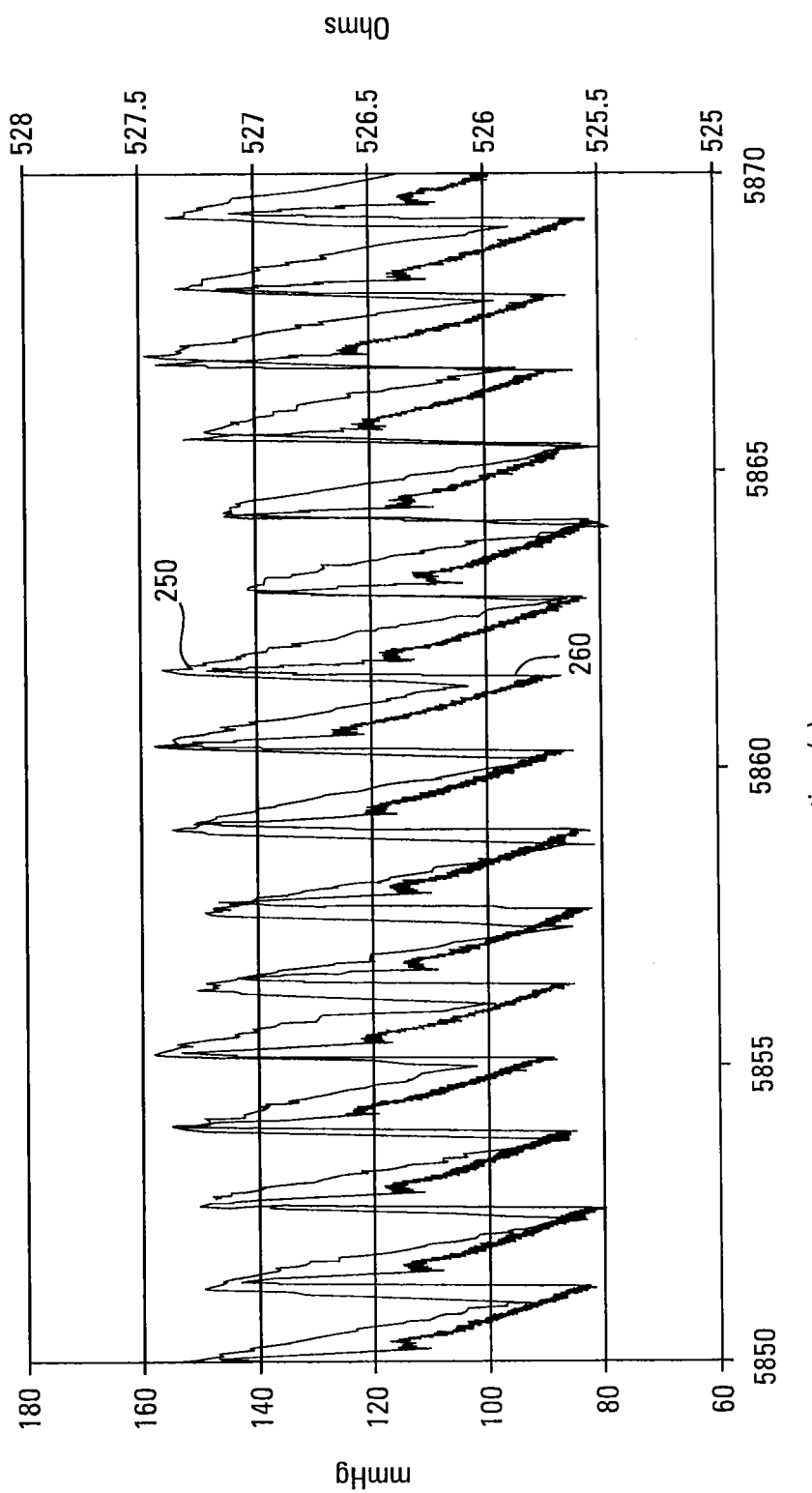
FIG. 6 is a graph depicting the correlation between vascular impedance and blood pressure, according to one embodiment of the present invention.

In one experiment, a precision LCR meter coupled to a pair of electrodes on the carotid sinus was used to obtain the impedance measurements. The electrodes were spaced circumferentially 120 degrees apart on the carotid sinus, with one electrode comprising an anode and the other comprising a cathode. Blood pressure was measured by a transducer temporarily implanted in the femoral artery. During the experiment, the frequency of the measurement signal ranged from 20 Hz to 2 MHz, and the amplitude ranged from 50 mV to 1V. The results of the experiment are depicted in FIG. 6. As can be seen, the vascular impedance 250 as measured through the electrodes closely correlates to blood pressure 260 as measured by the implanted pressure transducer. For the results depicted in FIG. 6, impedance was measured at a test frequency of 2 KHz and a constant voltage of 100 mV.

Figure 7A:
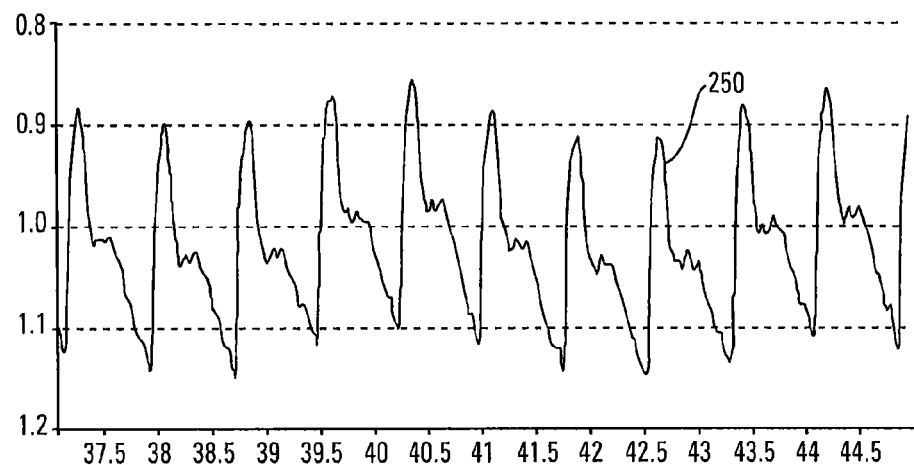
FIG. 7A is a graph depicting measured vascular impedance according to one embodiment of the present invention.
Figure 7B:
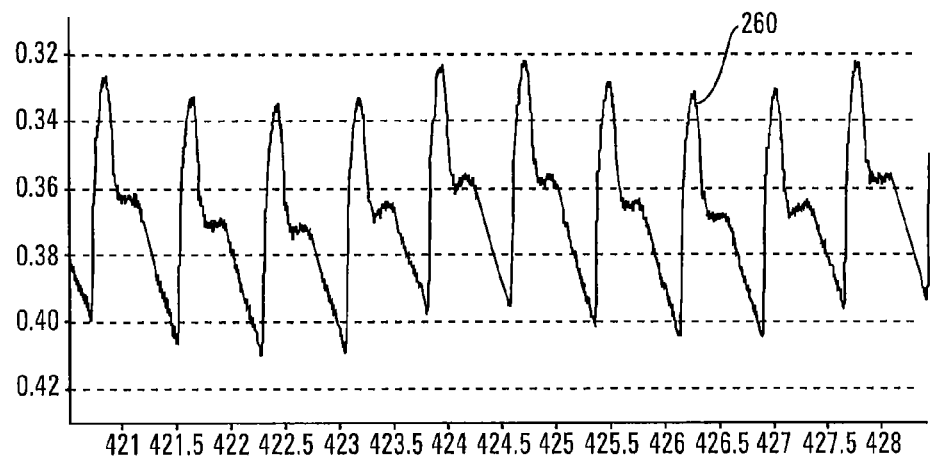
FIG. 7B is a graph depicting measured blood pressure according to one embodiment of the present invention.

In a still further experiment, a pair of electrodes 210 were implanted on the carotid artery, proximate the carotid sinus, with the electrodes spaced approximately 0.41 inches apart from one another along the vessel. A pressure transducer was temporarily implanted within the femoral artery to measure actual blood pressure. Measurement signals applied to electrodes 210 were on the order of 200 µA at 125 Hz, with a pulse width of 60 usec. The results of the experiment are depicted in FIGS. 7A and 7B, which illustrate the correlation between measured vascular impedance 250 and measured blood pressure 260. In some experiments it has been observed that measured impedance appears out of phase with measured blood pressure. Inversion of the vertical axis of the impedance plot, or conversion of measured impedance to conductance results in the measured signal being in phase with measured blood pressure. Conductance is the inverse of the sum of the alternating current impedance and the direct current impedance. Direct current impedance has been found to correlate to average blood pressure. Referring again to FIG. 7A, the vertical axis of the graph of vascular impedance 250 has been inverted to more clearly depict the correlation between impedance and blood pressure.

In one embodiment, suitable parameters for a measurement signal are generally on the order of hundreds of microamperes or tens of millivolts to two volts, at a frequency of 10 Hz to 200 Hz, with a pulse width of hundreds to tens of microseconds. A wide range of blood pressure can be accurately monitored, at least between 60 mmHg and 300 mmHg.

At time of implantation for use in a chronic application, tests may be conducted similar to the experiments described above, to establish a patient-specific correlation between blood vessel impedance and blood pressure. An external blood pressure cuff, or a temporarily implanted pressure transducer may be used to provide a blood pressure measurement that can be recorded and correlated to a measured impedance. The correlation is stored within the control system and used for chronic impedance measurements.

Further, in all embodiments discussed herein it may be desirable to obtain an absolute pressure reading, such as with an initial baseline pressure measurement. This baseline pressure measurement may be obtained with an external blood pressure cuff, an internal transducer sensor, a blood pressure catheter, or other similar devices. Periodic pressure measurements may be obtained after the baseline measurement to account for drift. A means for compensating for atmospheric pressure changes may also be included.

In addition to blood pressure, other physiologic parameters can be determined from the impedance measurement. For example, referring again to FIGS. 6 and 7A-7B, the time between pressure peaks in the monitored signal corresponds to the heart rate of the test subject, and the low-frequency component of the signal corresponds to respiration of the test subject.

Additional information about the patient, such as activity level, posture, and sleep state may also be determined from an impedance measurement. In one embodiment, the activity level of the patient may be determined from the impedance measurement. The hemodynamic system of the patient exhibits changes during periods of increased activity, for example, increased blood pressure and increased heart rate. By monitoring the blood pressure, heart rate, and/or other parameters, and detecting short term changes in those parameters, the activity level of the patient can be determined. Short term changes may be measured in seconds, or minutes.

In another embodiment, the posture or orientation of the patient may be determined from the impedance measurement. Referring to posture, when a patient moves from a supine position to an erect position, the body of the patient modifies one or more characteristics of cardiac and/or vascular function to accommodate for the change in the hemodynamic equilibrium of the patient, such as by activation or modulation of the baroreflex system of the patient to maintain a constant blood pressure in the carotid artery. By utilizing the impedance measurement system of the present invention alone or in combination with other sensors, changes in cardiac and/or vascular functions such as blood pressure, pressure waves, reflected waves, augmentation index, pulse wave velocity, heart rate, or heart rate variability, can be detected and measured so as to determined the posture of the patient.

In a further embodiment, the posture of the patient may be used in combination with other patient information to determine the sleep state of the patient. For example, a rise in blood pressure accompanied by a change in posture from horizontal to vertical may be an indication that the patient has woken from sleep.

Referring now to another embodiment, the impedance measurement system may be combined with or used in conjunction with a baroreflex therapy device having dedicated stimulation electrodes. In one embodiment, two or more measurement electrodes are implanted on or about a blood vessel, and communicably coupled to a controller, preferably the same controller as utilized by baroreflex therapy device. In another embodiment, the measurement electrodes are coupled to the baroreflex therapy device.

In one embodiment, the stimulation electrodes of the therapy device may be configured to conduct impedance measurements as well as provide therapy, such that a delivered therapy signal acts as both the therapy source and the driving measurement source. The same electrodes are therefore used to transmit the therapy signal (which also functions as the measurement signal) and to monitor the resultant signal as therapy is being delivered. The measurement sampling rate is therefore the same as the therapy rate. The electrodes can be positioned as two laterally spaced annular rings around the blood vessel in or about which baroreflex modulation device is implanted, such as the carotid sinus. Alternatively, the electrodes can be spaced apart along the longitudinal axis of the blood vessel.

In one embodiment, baroreflex modulation device utilizes a constant current therapy signal. Continuous therapy signals can include a constant pulse, a constant train of pulses, a triggered pulse and a triggered train of pulses. As the constant current therapy signal is being supplied to the output during therapy, the resultant voltage impressed across the electrode-tissue interface is monitored. The variation in the voltage represents changes in blood vessel volume in the area. The monitored signal is then amplified, filtered, and decoded and then digitally processed by control system 60 to obtain the measured values. Alternatively, the therapy signal voltage may be constant and the current of the resultant signal can be monitored. Impedance can then be determined from the voltage and current values, from which blood pressure and other physiologic parameters, such as heart rate and respiration, can be calculated. In one embodiment, the control system 60 can automatically calculate the physiological parameters from the measured values and display them to the treating physician or other user.

Increased sensitivity to the physiologic parameter being measured can be achieved by adjusting the rate of the measurement signal. The measurement signal must have a high enough frequency to effectively sample the intended signals. The measurement signal can be altered as desired to optimize the sampling rate for the higher frequency needs of blood pressure or lowered for slower moving signals, such as respiration. In one embodiment, the measurement signal is set to a short pulse width and a moderate frequency between 10 and 50 Hz. In one embodiment, a measurement frequency of 10 Hz may be adequate for monitoring respiration, 20 Hz for monitoring heart rate, and 20-50 Hz for blood pressure monitoring.

Figure 8:
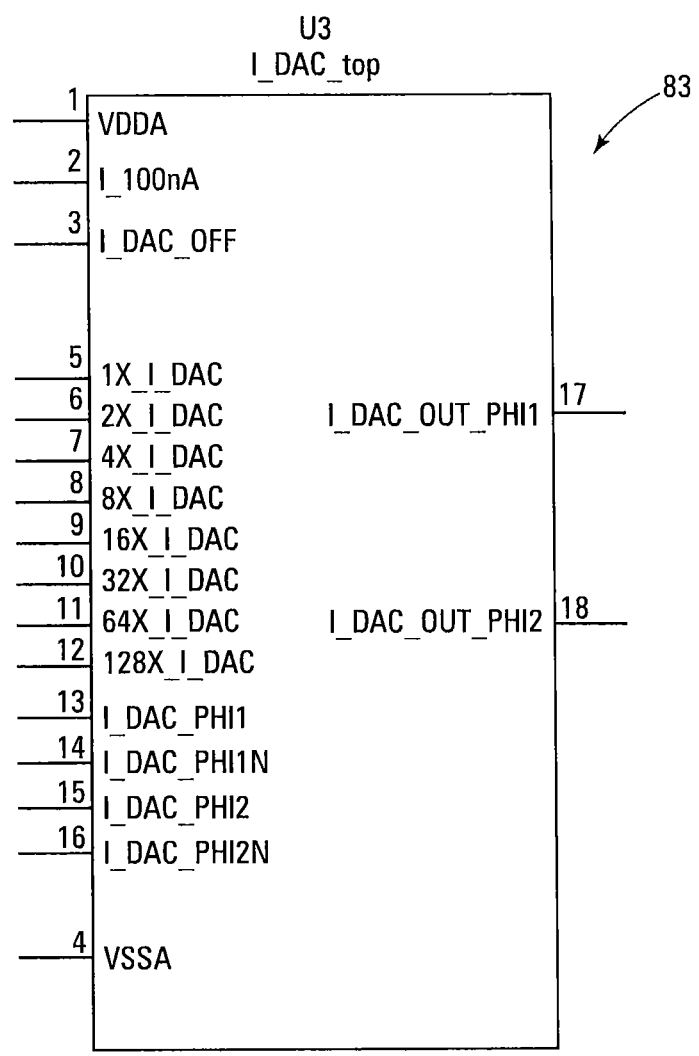
FIG. 8 is a block diagram of a current digital-to-analog converter input in accordance with the present invention.
Figure 9:
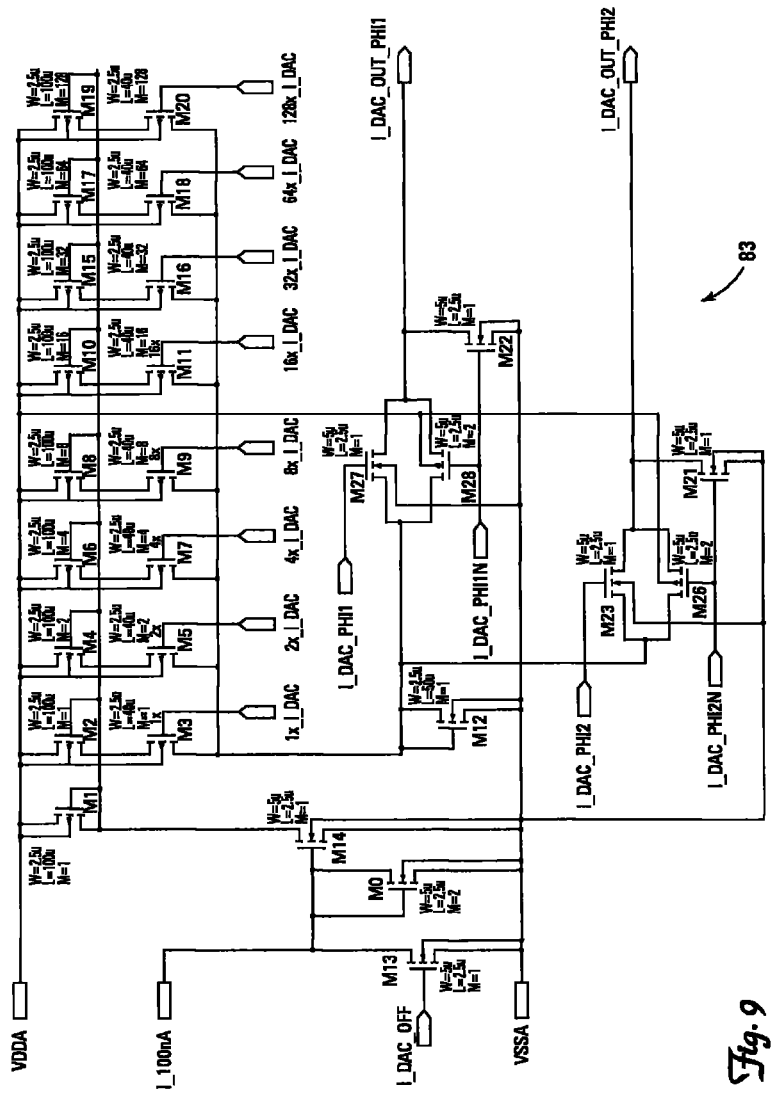
FIG. 9 is a schematic diagram of a current digital-to-analog converter input in accordance with the present invention.
Figure 10:
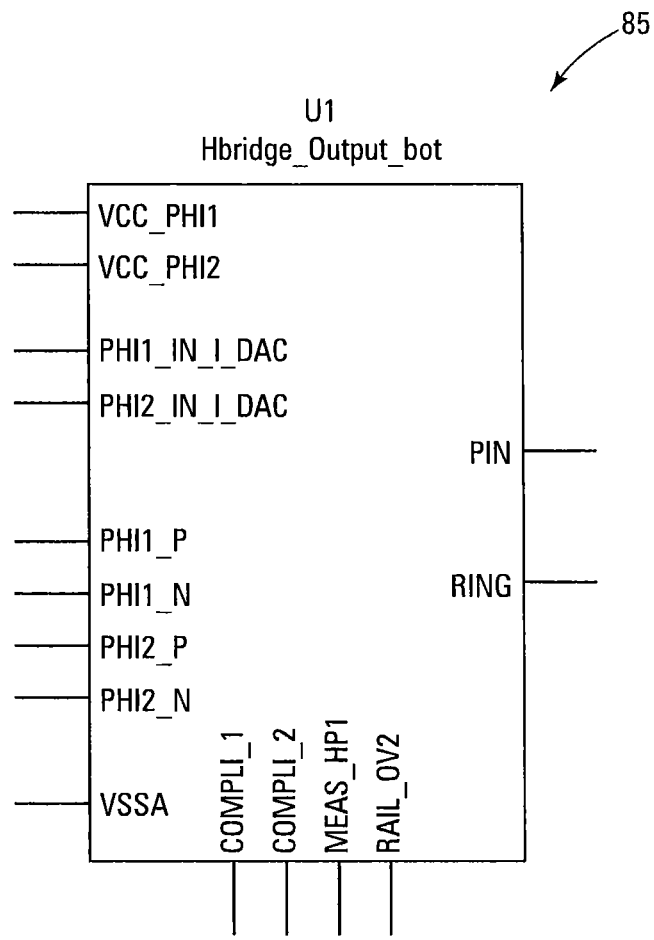
FIG. 10 is a block diagram of an H-bridge output in accordance with the present invention.
Figure 11:
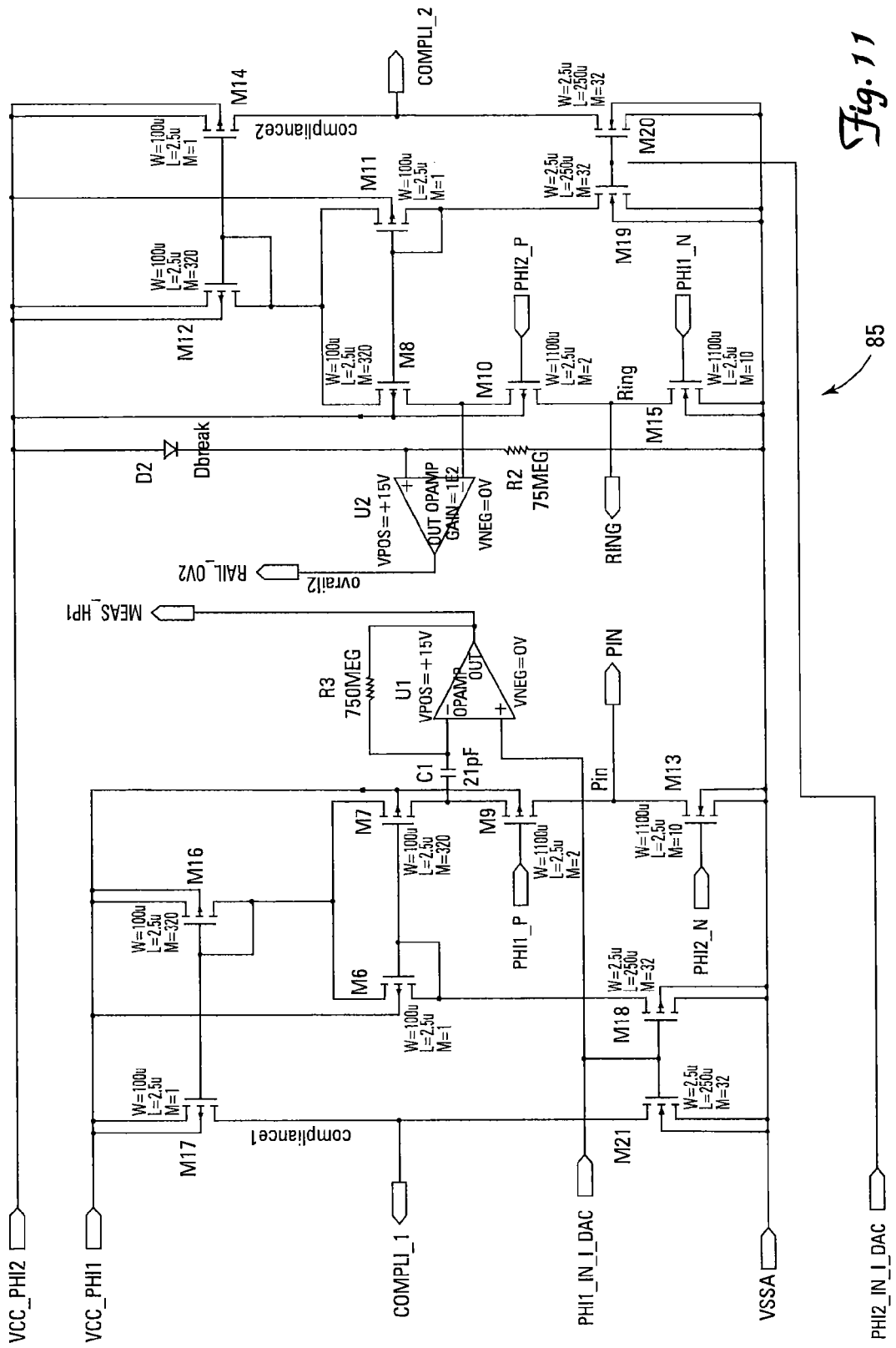
FIG. 11 is a schematic diagram of an H-bridge output in accordance with the present invention.

According to one embodiment, the baroreflex modulation device utilizes a constant current output circuit having a current digital-to-analog converter 83 input followed by an H-bridge output 85. A block diagram and a schematic diagram of the digital-to-analog converter 83 are depicted in FIG. 8 and FIG. 9, respectively, and a block diagram and a schematic diagram of the H-bridge 85 are depicted in FIG. 10 and FIG. 11, respectively.

Using the therapy signal as both the therapy source and the driving measurement source allows the therapy signal to be measured on a beat-by-beat or pace-by-pace basis. Real time or near real time monitoring of the therapy is therefore possible. Monitoring the physiological response of the patient in real time is advantageous in that it allows for continuous optimization of treatment.

Figure 12:
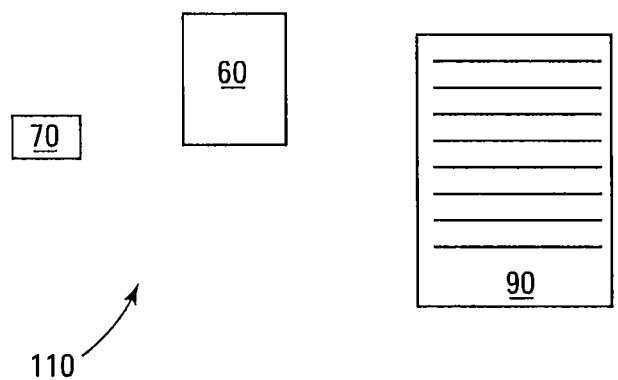
FIG. 12 is a diagram of a baroreflex therapy kit in accordance with the present invention.

In one embodiment, instructions for implanting a measurement system and/or therapy system in accordance with the various embodiments described herein in the form of printed or electronically, optically or magnetically stored information to be displayed, for example, are provided as part of a kit or assemblage of items prior to surgical implantation of the system. Referring to FIG. 12, in one embodiment a baroreflex therapy system can be provided to a user in a kit 110. Kit 110 may include a baroreflex modulation device 70 having one or more electrodes, a control system 60 operably coupleable to the baroreflex modulation device 70, and a set of instructions 90 recorded on a tangible medium for operating the system. Baroreflex modulation device 70 may be configured to conduct impedance measurements, or operably coupled to a set of measurement electrodes provided as part of kit 110. Kit 110 may be comprised of one or more hermetically sealed and sterilized packages. Instructions 90 may be provided as part of kit 110 or indications may be provided linking a user to electrically accessible instructions 90. In another embodiment, instructions for implanting the system in accordance with the various embodiments described herein are provided, for example, by a manufacturer or supplier of system, separately from providing the system, such as by way of information that is accessible using the Internet or by way of seminars, lectures, training sessions or the like.

In one embodiment, the health of the cardiovascular system of a patient can be determined by monitoring one or more physiologic parameters of a patient based on a vascular impedance measurement. For example, data relating to a vascular impedance measurement may be captured and stored for later review by a physician. Data may also be captured and stored for a pre-determined time until it is transmitted to or downloaded by a physician, or transmitted to an automated receiver that is accessible by a physician. Wireless telemetry systems known to those skilled in the art may be utilized to accomplish the communication of vascular impedance data.

In another embodiment, the effectiveness of a given therapy may be evaluated by monitoring one or more physiologic parameters of a patient based on a vascular impedance measurement. The delivered therapy may comprise a cardiac rhythm management (CRM) therapy. In such an embodiment, an implantable pulse generator is provided, having at least two leads. A first lead is implanted intravascularly and configured to deliver a CRM therapy. A second lead is coupled to a monitoring device according to one aspect of the present invention, the monitoring device having one or more electrodes and configured to measure vascular impedance. The monitoring device may be disposed intravascularly, extravascularly, or transvascularly, depending on the desired application. The measured vascular impedance is used to provide one or more patient parameters, upon which the CRM therapy may be adjusted or modified. Other delivered therapies may include neural stimulation and/or modulation therapies, renal therapies, drug delivery therapies, left ventricular assist devices, heart wraps, other mechanical therapies, thermal therapies, or any other therapy having a measurement component in addition to a therapy component.

In one embodiment, the extravascular measurement wrap may be implanted on the subclavian vein, or on another suitable vessel proximate to the location of an incision created during the implantation of an implantable pulse generator (IPG) associated with a cardiac rhythm management (CRM) device or neurostimulator device. Implantation of a CRM device typically involves the creation of a small subcutaneous pocket in the torso of a patient, and implantation of a lead in the heart via the vasculature of the patient, accessed at a location proximate the pocket for the IPG. Implanting an extravascular wrap during implantation of the IPG, at a location such as the subclavian vein that is accessible during the procedure, would reduce implant time as well as reduce patient trauma. Extravascular wrap may be operably coupled to a dedicated controller for performing necessary calculations and functions, with the dedicated controller operably communicable with the IPG of the CRM device, or extravascular wrap may be communicably coupled directly to the IPG of the CRM device. The CRM or neurostimulation therapy may be adjusted or modulated based on information received from an impedance measurement obtained by the extravascular wrap.

In another embodiment, multiple baroreflex modulation devices can be provided as part of a baroreflex modulation therapy system. In one embodiment, the sensing arrangement may comprise a separate baroreflex modulation device that is capable of delivering CRM. Additional disclosure pertaining to the combination of BAT devices and therapies with CRM devices and therapies that is relevant to the present invention can be found in Published U.S. Patent Application No. 2006/0004417 to Rossing et al., and Published U.S. Patent Application No. 2006/0074453 to Kieval et al., the disclosures of which are hereby incorporated by reference in their entireties.

Additional disclosure material that exemplifies at least a portion of the other features and functionality of the range of embodiments within the spirit and scope of the present invention can be found in Published U.S. Patent Application No. 2005/0154418 to Kieval et al., Published U.S. Patent Application No. 2005/0251212 to Kieval et al., and Published U.S. Patent Application No. 2006/0293712 to Kieval et al., the disclosures of which are hereby incorporated by reference in their entireties. Additional disclosure material relating to vascular anatomy and the cardiovascular system as it pertains to the present invention can be found in U.S. Pat. No. 6,522,926 to Kieval et al., the disclosure of which is hereby incorporated by reference.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A method of calibrating an implantable system, the system including a first electrode, a second electrode, and a control system coupled to the first and second electrodes, wherein the first and second electrodes are implanted in contact with a wall of a blood vessel of a patient, the method comprising:
    applying a measurement signal with the control system to the first electrode, the measurement signal having a known parameter;
    obtaining a resultant signal through the second electrode, the resultant signal having a resultant parameter;
    calculating impedance of the blood vessel based on the measurement signal and the resultant signal;
    contemporaneously obtaining a blood pressure measurement of the patient;
    comparing the impedance of the blood vessel to the blood pressure measurement to determine a patient-specific relationship between blood vessel impedance and blood pressure; and
    storing the patient-specific relationship in a memory of the control system.

2. The method of claim 1, wherein contemporaneously obtaining the blood pressure measurement is accomplished via a sphygmomanometer.

3. The method of claim 1, wherein contemporaneously obtaining the blood pressure measurement is accomplished via a temporarily implanted pressure transducer.

4. The method of claim 1, further comprising delivering a therapy signal from the control system, the therapy signal based at least in part on the patient-specific relationship stored in the memory of the control system.

5. The method of claim 4, wherein the therapy signal comprises the measurement signal.

6. The method of claim 1, further comprising storing the blood pressure measurement in the memory as a baseline blood pressure measurement.

7. The method of claim 1, further comprising:
    contemporaneously obtaining a second blood pressure measurement;
    calculating a subsequent impedance of the blood vessel based on a second measurement signal and a second resultant signal;

comparing the subsequent impedance and the second blood pressure measurement to the patient-specific relationship stored in the memory; and recalibrating the patient-specific relationship if the subsequent impedance of the blood vessel does not correlate to the second blood pressure measurement according to the patient-specific relationship.

8. The method of claim 1, wherein the measurement signal has a frequency between 10 Hz and 50 Hz.

9. The method of claim 1, wherein at least one of the first and second electrodes are implanted in contact with a blood vessel of a patient selected from the group consisting of: a carotid sinus, an aortic arch, a common carotid artery, a subclavian artery, a brachiocephalic artery, pulmonary artery, pulmonary vein, jugular vein, femoral artery, femoral vein, and a heart.

10. A method, comprising:

causing a system to be manufactured and made available to a user, the system including a first electrode, a second electrode, and a control system coupled to the first electrode and the second electrode;

providing instructions to the user, the instructions comprising:

implanting the system such that each of the first and second electrodes are implanted in contact with a wall of a blood vessel;

applying a measurement signal with the control system to the first electrode, the measurement signal having a known parameter;

obtaining a resultant signal through the second electrode, the resultant signal having a resultant parameter;

causing the control system to calculate an impedance of the blood vessel based on the measurement signal and the resultant signal;

contemporaneously obtaining a blood pressure measurement of the patient;

causing the control system to compare the impedance of the blood vessel to the blood pressure measurement to determine a patient-specific relationship between blood vessel impedance and blood pressure; and causing the control system to store the patient-specific relationship in a memory of the control system.

11. The method of claim 10, wherein contemporaneously obtaining the blood pressure measurement is accomplished via a sphygmomanometer.

12. The method of claim 10, wherein contemporaneously obtaining the blood pressure measurement is accomplished via a temporarily implanted pressure transducer.

13. The method of claim 10, the instructions further comprising causing the control system to deliver a therapy signal from the control system to at least one of the electrodes, the therapy signal based at least in part on the patient-specific relationship stored in the memory of the control system.

14. The method of claim 13, wherein the therapy signal comprises the measurement signal.

15. The method of claim 10, wherein the measurement signal has a frequency between 10 Hz and 50 Hz.

16. The method of claim 10, wherein the instructions are provided to the user and/or the control system.

17. The method of claim 10, wherein at least one of the first and second electrodes are implanted in contact with a blood vessel of a patient selected from the group consisting of: a carotid sinus, an aortic arch, a common carotid artery, a subclavian artery, a brachiocephalic artery, pulmonary artery, pulmonary vein, jugular vein, femoral artery, femoral vein, and a heart.

18. A method of determining a physiological parameter of a patient, comprising:

applying a measurement signal through a plurality of electrodes implanted in contact with a wall of a blood vessel of the patient, the measurement signal having a known parameter and a frequency between 10 Hz and 50 Hz;

obtaining a resultant signal through the plurality of electrodes, the resultant signal having a resultant parameter;

calculating impedance of the blood vessel based on the measurement signal and the resultant signal; and determining a physiological parameter based on the impedance of the blood vessel.

19. The method of 18, wherein the measurement signal has a frequency of about 10 Hz, and wherein the physiological parameter comprises respiration.

20. The method of 18, wherein the measurement signal has a frequency of about 20 Hz, and wherein the physiological parameter comprises heart rate.

21. The method of 18, wherein the measurement signal has a frequency between 20 Hz and 50 Hz, and wherein the physiological parameter comprises blood pressure.

* * * * *